United States Statutory Invention Registration [19]

[11] Reg. Number: H753

Hall et al. [43] Published: Mar. 6, 1990

[54] RIGIDIZED OXAZOLE DYES

[75] Inventors: John H. Hall, Carbondale, Ill.; Ronald A. Henry; Richard A. Hollins, both of Ridgecrest, Calif.

[73] Assignee: The United States of America as represented by the Secretary of the Navy, Washington, D.C.

[21] Appl. No.: 297,891

[22] Filed: Jan. 17, 1989

[51] Int. Cl.[4] ..... C07D 413/04

[52] U.S. Cl. ..... 546/270

[56] References Cited

U.S. PATENT DOCUMENTS

| | | | |
|---|---|---|---|
| 3,892,734 | 7/1975 | Okubo et al. | 260/240 D |
| 4,460,779 | 7/1984 | Borro | 548/217 |
| 4,506,368 | 3/1985 | Lee | 372/53 |

FOREIGN PATENT DOCUMENTS

| | | |
|---|---|---|
| 55-70834 | 5/1980 | Japan . |

*Primary Examiner*—John F. Terapane
*Assistant Examiner*—Chhaya Sayala
*Attorney, Agent, or Firm*—William C. Townsend; Melvin J. Sliwka

[57] ABSTRACT

The quaternary salts of rigidized 1,3-oxazole compounds of the formula:

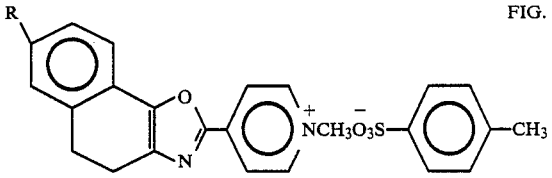

FIG. 1 where R is either H or $CH_3O$. The compounds are produced in a modified Robinson-Gabriel synthesis of oxazoles. These dyes are used in solution with non-interfering polar solvents, such as ethanol and $H_2O$, to form lasing media useful in dye lasers.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

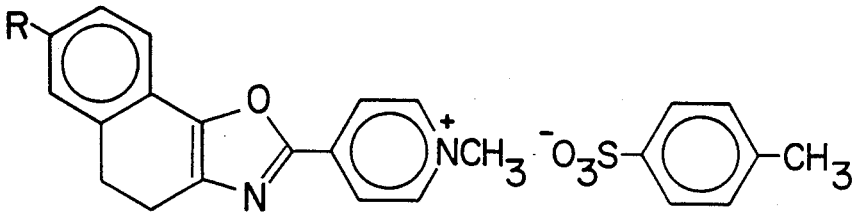

R = H, $CH_3O$

RIGIDIZED OXAZOLE DYES

CROSS-REFERENCE TO RELATED APPLICATION

This application is a substitute for application Ser. No. 06/808,380 filed Sept. 18, 1888 and now abandoned.

BACKGROUND OF THE INVENTION

1. Field of the Invention

This invention relates to rigidized 1,3-oxazoles and a method for their synthesis. Additionally, this invention relates to the use of rigidized 1,3-oxazoles to form lasing media useful in dye lasers.

2. Description of the Prior Art 2,5-Diaryl-1,3-oxazoles and certain salts derived from those compounds are useful as laser dyes. The synthetic methods available for the preparation of those compounds all involve multistep syntheses with relatively low overall yields. A one-step synthesis of 1,3-oxazoles is known. This synthesis involves the reaction of ketones with nitriles in the presence of cupric triflate as an oxidizing agent. In a typical procedure, the ketone is added dropwise to the cupric triflate in refluxing nitrile containing a trace of an acid catalyst. The oxazole forms a complex with the cuprous triflat by-product and must be separated by thermalization and vacuum distillation, steam distillation with excess benzonitrile, or extraction of the copper salts with concentrated ammonium hydroxide.

The one-step synthesis for the production of 1,3-oxazoles is limited to those cases where the nitrile can be used as the solvent. The procedure is unsuccessful with a 1:1 molar ratio of ketone to nitrile in ethyl acetate at room temperature, or in refluxing glyme or in refluxing diglyme. The use of extended reaction times in the synthesis at 1:1 mole ratios results in the formation of polymeric materials.

SUMMARY OF THE INVENTION

An object of this invention is to provide rigidized 1,3-oxazoles and their quaternary salts for use with non-interfering solvents to form lasing media useful in dye lasers.

Yet another object of this invention is to provide a method of synthesizing rigidized 1,3-oxazoles and their quaternary salts.

According to the present invention, 1,3-oxazoles are produced with an ethylene bridge between the 4-position of the 1,3-oxazole and the ortho position of the aromatic ring. These compounds are prepared from the corresponding 1-tetralones by conversion to the 2-oxime with butyl nitrite. Catalytic reduction in acid gives the 2-amino-1-tetralone hydrochloride which is reacted with isonicotinoyl chloride to give the amide. Ring closure to the 1,3-oxazole with phosphorus oxychloride gives the rigidized 1,3-oxazole. This particular ring closure step is a modified Robinson-Gabriel syntheses of oxazoles by the cyclodehydration of acylaminoketones. Methylation of the rigidized 1,3-oxazole with methyl p-toluenesulfonate gives the quaternary salts having the formula shown in FIG. 1.

BRIEF DESCRIPTION OF THE DRAWINGS

FIG. 1 shows the structures of 2-(4-N-methylpyridinium)-4,5- dihydro-naphth[2,1-d]-1,3-oxazole p-toluenesulfonate and 2-(4-N-methylpyridinium)-4,5-dihydro-6-methoxynaphtho[2,1-d]-1,3oxazole p-toluenesulfonate.

FIG. 2 shows the structures of 2-(4-pyridyl)-4,5-dihydronaphtho[2,1-d]-1,3-oxazole and 2-(4-pyridyl)-4,5-dihydro6-methoxynaphtho[2,1-d]-1,3-oxazole.

DETAILED DESCRIPTION OF THE INVENTION

The synthetic route for preparing 1,3-oxazoles with an ethylene bridge between the 4-position of the 1,3-oxazole and the ortho position of the aromatic ring is outlined generally as follows, starting with the preparation of precursors used in the synthesis.

First, the 1-tetralones are converted to the oximes using a procedure which is essentially that reported by W. G Reinfenrath and D. S. Fries, *J. Chem. Soc., C,* 288 (1967); F. Zymalkowski and H. J. Rimek, *Arch Pharm.* (*Weinheim. Ger.*). v. 294, 581 (1961). 1-tetralone is converted to the 1-tetralone-2-oxime and 6-methoxy-1-tetralone is converted to 6-methoxy-1-tetralone-2-oxime. The oxime is then catalytically reduced in acid to give the 2-amino-1-tetralone hydrochloride or the 6-methoxy-2-amino-1-tetralone hydrochloride. The tetralone hydrochloride is then reacted with isonicotinic acid chloride to give the isonicotinamide of 2-amino-1-tetralone or the isonicotinamide of 6-methoxy-2-amino-1-tetralone.

According to the invention, the isonicotinamide of 2-amino-1tetralone and isonicotinamide of 6-methoxy-2-amino-1-tetralone precursors are transformed into oxazoles by cyclodehydration of acylaminoketones. Phosphorus oxychloride is the preferred cyclodehydration reagent. This reaction is a modified Robinson-Gabriel synthesis of oxazoles. Oxazoles with the structure shown in FIG. 1 are produced.

The oxazoles are then methylated with methyl p-toluenesulfonate to give the corresponding quaternary salts.

The synthesis of relevant precursors used in the invention as well as the modified Robinson-Gabriel synthesis of oxazoles is illustrated in the following examples.

EXAMPLE 1

In this example the oxime was formed from the corresponding tetralone.

1-tetralone-2-oxime

Potassium (12.5 g. 0.32 mole) was dissolved in t-butanol (200 ml) with stirring and refluxing. Ether (500 ml) was added, followed by dropwise addition of 1-tetralone (43.0 g, 0.294 mole) over a 10 minute period. Butyl nitrite (37 g, 0.36 mole) was added over a period of one hour. The solution was chilled with ice to form a precipitate. The salts were filtered and washed with ether. They were slurried with 400 ml of water and then 40 ml of concentrated HCl was added. The oxime was extracted with ether (800 ml) and then the ether was dried with $MgSO_4$ and concentrated to 100 ml. The resulting solid was filtered to give a crude yield of 24.3g (47%).

Recrystallization from cold 95% ethanol gave 18.7 g of purified material, mp 142–144 g (47%)

6-methoxy-1-tetralone oxime

In 60 ml of refluxing t-butanol was dissolved 3.84 g (0.0985 mole) of potassium. Ether (150 ml) was added followed by 15.87 g (0.09 mole) of 6-methoxy-1-tetralone. Butyl nitrite (11.1 g, 0.0932 mole) was added dropwise with stirring over a period of 30 minutes. The insoluble salts were filtered and washed with ether. They were slurried with 180 ml of water and then 15 ml of Concentrated HCl was added. The initially formed oil solidified. The solid was filtered and washed with water. Recrystallization of the still damp product from 250 ml of ethanol gave 8.86 g. Concentration of the filtrate to ⅓ volume gave 2.06 g additional material. Total yield 10.92 g (59%). A second recrystallization gave an analytical sample, mp 168°-171° dec.

EXAMPLE 2

In this example the oximes are reduced by acid catalyst to give the corresponding tetralone hydrochloride.

2-amino-1-tetralone hvdrochloride 1-tetralone-2-oxime (13.15 g, 0.07506 mole) was placed in 130 ml of methanol and 0.5 g of Pd-$BaSO_4$ catalyst was added. To this was added a solution of 13 ml of concentrated HCl in 65 ml of $H_2O$ and 130 ml of methanol. The mixture was hydrogenated at 50 psi for 1 hour and 20 minutes at which point there was no further uptake. The catalyst was filtered. The filtrate was evaporated to dryness and the solid (14.2 g) was recrystallized from ethanol to give 5.37 g. Concentration of the filtrate gave an additional 2.08 g. Total yield was 7.45 g (50%). Further concentration of the above filtrate gave a different hydrochloride.

The 2-amino-1-tetralone hydrochloride obtained above wa still grey. It had to be recrystallized from ethanol or i-propyl alcohol containing a small amount of HCl until the product was completely white. The grey color is due to the presence of 2-amino-1-naphthol hydrochloride which is rapidly oxidized in air.

6-methoxy-2-amino-1-tetralone hydrochloride 6-methoxy-1-tetralone-2-oxime (8.01 g, 0.0390 mole) was placed in a solution of 240 ml of methanol, 32 ml of $H_2O$ and 8 ml of concentrated HCl. To this was added 0.5 g of Pd-$BaSO_4$ catalyst. The mixture was hydrogenated at 50 psi for 105 minutes. The catalyst was filtered and the filtrate was evaporated to dryness. The residue was recrystallized from 180 ml of i-propyl alcohol containing 5 ml of concentrated HCl. Chilling this mixture in ice gave 5.99 g of crude hydrochloride. The solid at this stage was grey due to the presence of some 6-methoxy-2-amino-1-naphthol hydrochloride. A second recrystallization from ethanol removed the grey color and gave 3.00 g (34% yield), mp 217°-218° dec.

EXAMPLE 3

In this example the 2-amino-1-tetralone hydrochlorides are reacted with isonicotinoyl chloride to give the amide.

Isonicotinamide of 2-amino-1-tetralone

Isonicotinic acid (1.47 g, 0.012 mole) was refluxed with 5 ml of thionyl chloride for one hour. The excess thionyl chloride was removed under vacuum and the resulting acid chloride added all at once to a solution of 1.97 g (0.01 mole) of 2-amino-1-tetralone hydrochloride in 26 ml of pyridine. The mixture became warm (45° C.) and was then stirred for a few minutes to get all of the solid in solution. The mixture was then allowed to cool and stand at room temperature for 2 hours. The pyridine was removed under vacuum. The residue was treated with 60 ml of benzene and 40 ml of $H_2O$. The solution was made basic with 10% sodium hydroxide. The benzene layer was separated, washed with water and dried over magnesium sulfate. Evaporation gave 2.1 g of crude solid. Recrystallization from a concentrated benzene solution gave 1.32 g (50% yield) of the amide. A second recrystallization from benzene gave an analytical sample, mp 14.5°-146.5° C.

Isonicotinamide of 6-methoxy-2-amino-1-tetralone

Isonicotinic acid (2.20 g, 0.0179 mole) and thionyl chloride (7.5 ml) were refluxed for one hour. The excess thionyl chloride was removed under vacuum. The resulting acid chloride was added to a solution of 3.40 g (0.0149 mole) of 6-methoxy-2-amino-1-1-tetralone hydrochloride in 60 ml of pyridine. The solution was stirred and warmed slightly to get everything dissolved. After standing for 2 hours, the pyridine was removed under vacuum. The residue was treated with 15 ml of ethanol and 10 ml of water. The solution was made basic with 10% KOH. The resulting precipitate was filtered and washed thoroughly with water; yield of amide 2.30 g (43%).

EXAMPLE 4

In this example the cyclodehydration of the acylaminoketones takes place via a modified Robinson-Gabriel synthesis of oxazoles. The oxazoles produced by the following procedures have the structure shown in FIG. 2.

2-(4-pyridyl)-4.5-dihydro-naphtho[2,1-d]-1,3-oxazole

The isonicotinamide of 2-amino-1-tetralone (1.14 g, 0.00429 mole) was placed in 12 ml of phosphorus oxychloride (phosphoryl chloride) and refluxed for 19 hours. The amide dissolved during this period of time. The excess reagent was removed under vacuum. The residue was treated with 12 ml of ethanol and 5 ml of water. The mixture was made basic with 10% KOH. On cooling, the product precipitated and was filtered to give 0.77 g (72% yield) of the oxazole, mp 129°-130° C. $^1H$ NMR(δ, $CDCl_3$): 3.10, 4H, $A_2B_2$; 7.3-7.9, 4H, m; 8.93, 4H, $A_2B_2$.

2-(4-Pyridyl)-4,5-dihydro-6-methoxynaphtho[2,1-d]-1,3-oxazole

The isonicotinamide of 6-methoxy-2-amino-1-tetralone (1.55 g, 0.00524 mole) was refluxed for 44 hours in 15 ml of phosphorus oxychloride (phosphoryl chloride). The excess reagent was removed under vacuum. The resulting residue was dissolved in 50 ml of 1:1 ethanol-water and the mixture made basic with 10% KOH. The precipitated solid was filtered to give 1.26 g of the product as fine needles, (86% yield). Recrystallization from i-propyl alcohol gave an analytical sample, mp 158°-158.5° C. $^1H$ NMR (δ, $CDCl_3$) 8.10, 4H, AzBz; 8.93, 3H, s; 8.8-7.8, 3H, m; 8 08, 8.95, 4H, $A_2B_2$.

EXAMPLE 5

In this example, the oxazole is methylated with methyl P-toluenesulfonate to form the quaternary salt. The compounds produced by the following procedures have the structure shown in FIG. 1.

2-(4-N-methylpyridinium)-4,5-dihydro-naphtho[2.1-d]1,3-oxazole p-toluenesulfate The oxazole (0.91 g, 0.00367 mole) was dissolved in 18 ml of dichloroethane and 0.82 g (0.00440 mole) of methyl p-toluenesulfate was added. The mixture was refluxed for 18 hours. On cooling to room temperature the salt crystallized. The salt was filtered, washed with ether and dried to give 1.57 g (91 % yield) of product as the dihydrate. Recrystallization from i-propyl alcohol gave an analytical sample, mp 182°–183.5° C. H NMR(δ, $CDCl_3$): 2.23, 3H, s; 2.50, 4H, bs ($H_2O$ of hydration); 3.00, 4H, $A_2B_2$; 8.22, 9.19, 4H, $A_2B_2$; 7.1–7.8, 4H, m.

2-(4-N-methylpyridinium)-4,5-dihydro-6-methoxynaphtho[2.1-d]-1,3-15 oxazole p-toluenesulfonate The oxazole (0.82 g, 0.00291 mole) was placed in 18 ml of dichloroethane and 0.65 g (0.0350 mole) of methyl p-toluenesulfonate was added. The solution was refluxed for 18 hours. The solution was cooled slightly and equal volume of ether was added. The precipitated solid was filtered and washed with ether to give 1.32 g. Recrystallization from i-propyl alcohol gave 0.92 g (63% yield) of the product as a dihydrate. A second recrystallization gave an analytical sample, mp 210°–212° C.$^1$H NMR (δ, $CDCl_3$): 2.23, 3H, s; 2.42, 4H, bs ($H_2O$ of hydration); 2.97, 4H, $A_2B_2$; 8.18, 9.10, 4H, $A_2B_2$; 8.7–8.9, 7.2–7.8, 8Hm m.

Table I shows the Fluorescence Wavelengths of the oxazoles and the quaternary salts when used with various solvents:

TABLE I

| FLUORESCENCE WAVELENGTH | | |
|---|---|---|
| Compound | Solvent | Fluorescence,nm |
| 8a | Ethanol | 434 |
| " | 1:1 Ethanol $H_2O$ | 438 |
| " | 0.5 M HC104 in Ethanol | 516 |
| 9a | Ethanol | 522,308 |
| " | 1:1 Ethanol $H_2O$ | 520,308 |
| 8b | Ethanol | 463 |
| " | 1:1 Ethanol $H_2O$ | 476 |
| " | 0.5 M HC104 in Ethanol | 579 |
| 9b | Ethanol | 582,306 |
| " | 1:1 Ethanol $H_2O$ | 588,312 |

8a 2-(4-pyridyl)-4,5-dihydro-naphtho[2,1-d]-1,3-oxazole
9a 2-(4-N—methylpyridinium)-4,5-dihydro-naphtho[2,1-d]-1,3-oxanzole p-toluenesulfonate
8b 2-(4-pyridyl)-4,5-dihydro-6-methoxynaphtho[2,1-d]-1,3-oxazole
9b 2-(4-N—methylpyridinium)-4,5-dihydro-6-methoxynaphtho[2,1-d]-1,3-oxazole p-toluenesulfonate Table II shows the theoretical and analytical results of elemental analysis for the oxazoles and the quaternary salts.

TABLE II

| ANALYTICAL RESULTS | | | | | | | | | |
|---|---|---|---|---|---|---|---|---|---|
| | | Theoretical | | | | Found | | | |
| Compound | Formula | % C | % H | % N | % Cl or S | % C | % H | % N | % Cl or S |
| 8a | $C_{16}H_{12}N_2O$ | 77.40 | 4.87 | 11.28 | | 77.46 | 5.18 | 11.07 | |
| 8b | $C_{17}H_{14}N_2O_2$ | 73.37 | 5.07 | 10.07 | | 73.38 | 4.85 | 9.97 | |
| 9a | $C_{24}H_{22}N_2O_4S$ | 66.34 | 5.10 | 6.45 | 7.38 | 66.03 | 5.22 | 6.31 | 7.42 |
| 9b | $C_{25}H_{26}N_2O_6S^a$ | 62.22 | 5.43 | 5.81 | 6.64 | 62.26 | 5.27 | 5.69 | 6.93 |

[a]A monohydrate

Obviously, many modifications and variations of the present invention are possible. It should be understood, that, within the scope of the appended claims, the invention may be practiced otherwise than as specifically described.

What is claimed is:

1. As a composition of matter 2-(4-N-methylpyridinium)-4,5-dihydronaphtho [2,1-d]-1,3-oxazole p-toluenesulfonate.

2. As a composition of matter 2-(4-N-methylpyridinium)-4,5-dihydro6-methoxynaphtho[2,1-d]-1,3-oxazole p-toluenesulfonate.

3. A method for producing 2-(4-pyridyl)-4,5-dihydronaphtho[2,1-d]-1,3-oxazole by a modified Robinson-Gabriel synthesis of oxazoles, the improvement comprising the steps:

mixing the isonicotinamide of 2-amide-1-tetralone with phosphorus oxychloride;

refluxing said mixture;

removing the excess reagent and isolating a residue;

forming a solution of said residue, ethanol and water;

making said solution said residue, ethanol and water;

making said solution basic by adding a hydroxide; and precipitating the oxazole by cooling said basic solution and then removing said oxazole.

4. A method of preparing the quaternary salt 2-(4-N-methyl-2-pyridinium)-4,5-dihydro-naphtho[2,1-d]-1,3-oxazole p-toluenesulfonate from 2-(4-pyridyl)-4,5-dihydro-naphtho [2,1-d]-1,3-oxazole comprising the steps:

dissolving said oxazole in a solution of dichloroethane and methyl p-toluenesulfonate;

refluxing said solution; and crystallizing the product by cooling said solution.

5. A method for producing 2-(4-pyridyl)-4,5-dihydro-6-methoxynaphtho[2,1-d]-1,3-oxazole by a modified Robinson-Gabriel synthesis of oxazoles, the improvement comprising the steps:

mixing the isonicotinamide of 6-methoxy-2-amino-1-tetralone with phosphorus oxychloride;

refluxing said mixture;

removing the excess reagent and isolating a residue;

forming a solution of basic by adding a hydroxide; and precipitating the oxazole by cooling said basic solution and then removing said oxazole.

6. A method for producing the quaternary salt 2-(4-N-methylpyridinium)-4,5-dihydro-6-methoxynaphtho[2,1-d]1,3-oxazole p-toluenesulfonate from 2-(4-pyridyl)-4,5-dihydro-6-methoxynaphtho[2,1-d]-1,3-oxazole comprising the steps:

dissolving said oxazole in a solution of dichloroethane; and methyl p-toluenesulfonate;

refluxing said solution; and crystallizing the product by cooling said solution.

* * * * *